US012605193B2

(12) United States Patent
Hansen

(10) Patent No.: US 12,605,193 B2
(45) Date of Patent: Apr. 21, 2026

(54) MINIMALLY INVASIVE STERNAL FRACTURE REPAIR

(71) Applicant: Adam J. Hansen, Bridgeport, WV (US)

(72) Inventor: Adam J. Hansen, Bridgeport, WV (US)

( * ) Notice: Subject to any disclaimer, the term of this patent is extended or adjusted under 35 U.S.C. 154(b) by 271 days.

(21) Appl. No.: 18/544,623

(22) Filed: Dec. 19, 2023

(65) Prior Publication Data

US 2024/0197374 A1 Jun. 20, 2024

Related U.S. Application Data

(60) Provisional application No. 63/433,846, filed on Dec. 20, 2022.

(51) Int. Cl.
| | |
|---|---|
| *A61B 17/80* | (2006.01) |
| *A61B 17/86* | (2006.01) |
| *A61B 17/00* | (2006.01) |
| *A61B 17/56* | (2006.01) |
| *A61B 17/68* | (2006.01) |

(52) U.S. Cl.
CPC ...... *A61B 17/8076* (2013.01); *A61B 17/8004* (2013.01); *A61B 17/8023* (2013.01); *A61B 17/808* (2013.01); *A61B 17/8085* (2013.01); *A61B 17/8665* (2013.01); *A61B 2017/00238* (2013.01); *A61B 2017/564* (2013.01); *A61B 2017/681* (2013.01)

(58) Field of Classification Search
CPC .............. A61B 17/8004; A61B 17/823; A61B 17/8061; A61B 17/8076; A61B 17/8085; A61B 17/7077; A61B 17/8665; A61B 17/66; A61B 2017/681; A61B 2017/564
See application file for complete search history.

(56) References Cited

U.S. PATENT DOCUMENTS

| | | | |
|---|---|---|---|
| 5,911,701 A | 6/1999 | Miller | |
| 7,635,365 B2 * | 12/2009 | Ellis ................... | A61B 17/8076 |
| | | | 606/71 |
| 8,632,573 B2 * | 1/2014 | Ellis ................... | A61B 17/8076 |
| | | | 606/280 |

(Continued)

FOREIGN PATENT DOCUMENTS

| | | |
|---|---|---|
| EP | 3062747 A1 | 9/2016 |
| GB | 2558433 A | 7/2018 |

(Continued)

*Primary Examiner* — Anu Ramana
(74) *Attorney, Agent, or Firm* — Thomas | Horstemeyer, LLP

(57) ABSTRACT

Embodiments of an adjustable rib plate apparatus for repairing a fractured sternum are disclosed. The apparatus has a bridge plate, a first sternal plate, and a second sternal plate. The first and second sternal plates each have screw holes. The first and second sternal plates are attached to the first and second sternal parts via screws installed in the screw holes. The bridge plate also has elongated unthreaded screw holes and is installed with screws over respective parts of the sternal plates. The bridge plate overlaps respective parts of the first and second sternal plates so that the elongated screw holes are in sufficient alignment with underlying screw holes associated with the sternal plates to enable the bridge plate to move during installation of the apparatus.

17 Claims, 11 Drawing Sheets

(56)                    References Cited

U.S. PATENT DOCUMENTS

| | | | |
|---|---|---|---|
| 8,728,133 B2 | 5/2014 | Fell | |
| 8,974,504 B2 * | 3/2015 | Hess ................. | A61B 17/8028 |
| | | | 606/282 |
| 9,775,657 B2 * | 10/2017 | Bernstein ............ | A61B 17/863 |
| 10,022,169 B2 * | 7/2018 | Waizenegger ..... | A61B 17/8076 |
| 10,159,515 B2 * | 12/2018 | Ehmke .............. | A61B 17/8085 |
| 10,307,180 B2 | 6/2019 | Weitzman | |
| 10,342,583 B2 * | 7/2019 | Wallenstein ....... | A61B 17/8009 |
| 11,083,504 B2 * | 8/2021 | Bernstein .............. | A61B 90/92 |
| 2004/0147934 A1 | 7/2004 | Kiester | |
| 2008/0140128 A1 | 6/2008 | Smisson | |
| 2009/0163960 A1 * | 6/2009 | Binder .............. | A61B 17/1728 |
| | | | 606/280 |
| 2017/0035444 A1 | 2/2017 | Carrison | |
| 2019/0099207 A1 | 4/2019 | Houff | |
| 2021/0251671 A1 | 8/2021 | Madey | |

FOREIGN PATENT DOCUMENTS

| | | | |
|---|---|---|---|
| WO | 1996039956 A1 | 12/1996 | |
| WO | 2005020800 A2 | 3/2005 | |
| WO | 2014150858 A1 | 9/2014 | |
| WO | 2020123996 A1 | 6/2020 | |

* cited by examiner

MINIMALLY INVASIVE STERNAL FRACTURE REPAIR

CROSS-REFERENCE TO RELATED PATENT APPLICATION

This application claims the benefit of and priority to U.S. provisional application No. 63/433,846, filed on Dec. 20, 2022, which is incorporated herein by reference.

FIELD OF THE INVENTION

The invention generally relates to thoracic orthopedic surgery, and more particularly, to apparatus and methods for performing a minimally invasive sternal fracture repair using fixation.

BACKGROUND OF THE INVENTION

FIG. 1 illustrates a typical sternal fracture 11 in a human rib cage 13. Usually, a fracture occurs with trauma in a transverse or oblique fashion. FIG. 2 shows an example of a fracture 11' that is slightly oblique. When a sternal fracture is sustained, often the two fragments of the sternum overlap each other, as shown in FIG. 2. One sternal fragment becomes displaced posteriorly, and the other becomes displaced anteriorly. This orientation occurs randomly. It can result in either fragment being overlapped or underlapped. Oftentimes, the anterior and posterior bony tables of the two fragments become telescoped on each other as well.

SUMMARY OF THE INVENTION

Various embodiments are disclosed of apparatus and methods for performing a minimally invasive sternal fracture repair using fixation with an adjustable rib plate apparatus.

One embodiment, among others, is an adjustable rib plate apparatus having a bridge plate and first and second sternal plates. The first and second sternal plates each have an elongated body with opposing sides that are generally planar, and the opposing sides have a periphery defined by opposing side edges and opposing ends. The elongated bodies of each have a plurality of screw holes. The first and second sternal plates are attached to the first and second sternal parts via screws installed in the screw holes.

The bridge plate also has an elongated body with opposing sides that are generally planar, and the opposing sides having a periphery defined by opposing side edges and opposing ends. The elongated body has a plurality of screw holes, preferably although not necessarily elongated screw holes. The bridge plate overlaps respective parts of the first and second sternal plates so that its plurality of screw holes is in sufficient alignment with underlying screw holes associated with the first and second sternal plates to enable the bridge plate to be installed over the sternal plates via screws.

Another embodiment, among others, is a sternal retractor that can be used to install the adjustable rib plate apparatus that was described above. The sternal retractor generally includes a later control arm and first and second arms that extend from it More specifically, the first arm has a plurality of elongated first arm members connected together in a first series via a plurality of single axis joints. The first series having a distal end and a proximal end. The first arm has a first foot plate attached to the distal end via a first universal joint. The first foot plate having a means for detachably mounting the first arm to a first sternal plate.

The second arm has a plurality of elongated second arm members connected together in a second series via a plurality of single axis joints. The second series also has a distal end and a proximate end. The second arm has a second foot plate attached to the distal end via a second universal joint. The second foot plate has a means for detachably mounting the second arm to a second sternal plate.

The lateral control arm connects to the first and second arms at their respective proximate ends. The lateral control arm has a rack and pinion mechanism that enables lateral movement of the lateral control arm to shorten and lengthen a lateral distance between the first and second arms. The rack and pinion mechanism is capable of being locked and unlocked to prevent and permit respectively the lateral movement.

Another embodiment, among others, is a method for repairing a sternal fracture involving use of the previously described adjustable rib plate apparatus and the sternal retractor. The method can be summarized by the following steps: (a) temporarily attaching the first and second foot plates of the sternal retractor to the first and second sternal plates, respectively; (b) mounting the first and second sternal plates to respective first and second parts of the fractured sternum; (c) aligning the first and second parts of the fractured sternum by adjusting the sternal retractor; (d) mounting the bridge plate over the first and second sternal plates to secure together the bridge plate, the first and second sternal plates, and the first and second sternal parts; and (e) de-attaching the sternal retractor from the first and second sternal plates.

Other embodiments, apparatus, systems, methods, features, and advantages of the present invention will be apparent to one with skill in the art upon examination of the following drawings and detailed description. It is intended that all such additional embodiments, apparatus, systems, methods, features, and advantages be included within this disclosure, be within the scope of the present invention, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION OF EMBODIMENTS

The present disclosure provides an adjustable sternal plate apparatus that not only can distract the sternal fragments from an overlapped position, but can also elevate the one that is depressed and then compress the two fragments as they are stabilized together. Further stated, the adjustable sternal plate apparatus can distract, elevate, and compress.

Figure 1:
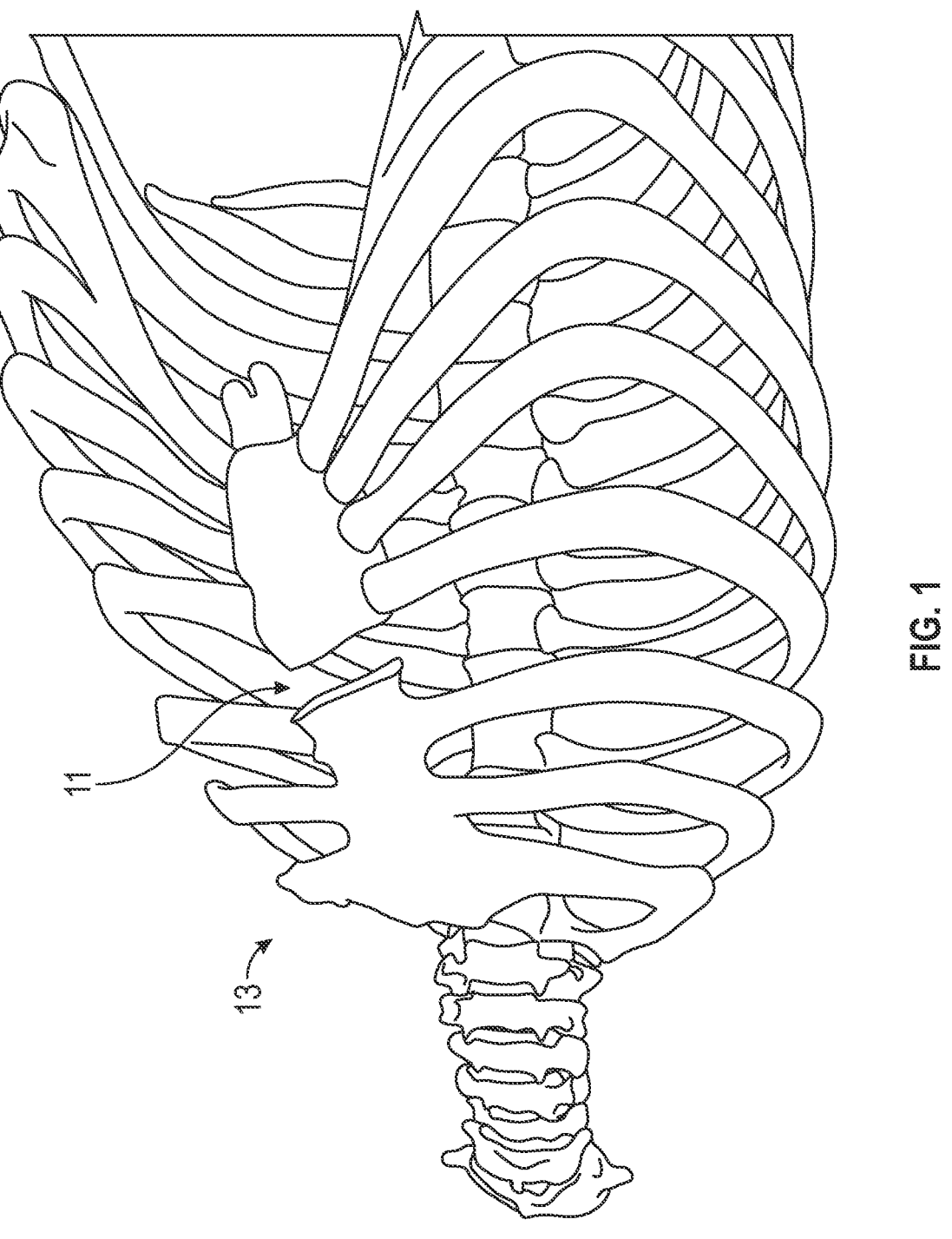
FIG. 1 is a view of a typical sternal fracture associated with a human ribcage.
Figure 2:
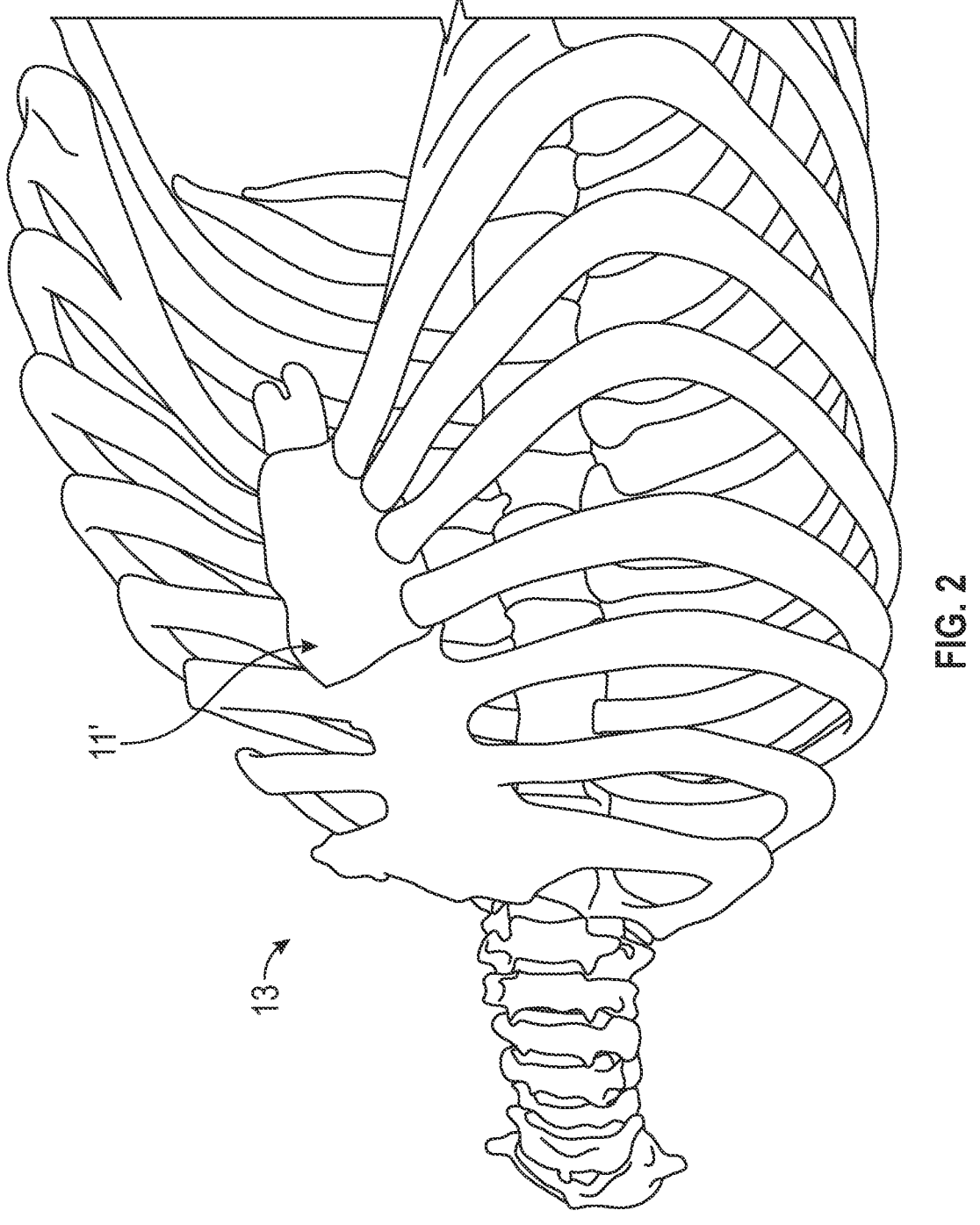
FIG. 2 is a view of a sternal fracture that has become slightly oblique.
Figure 3:
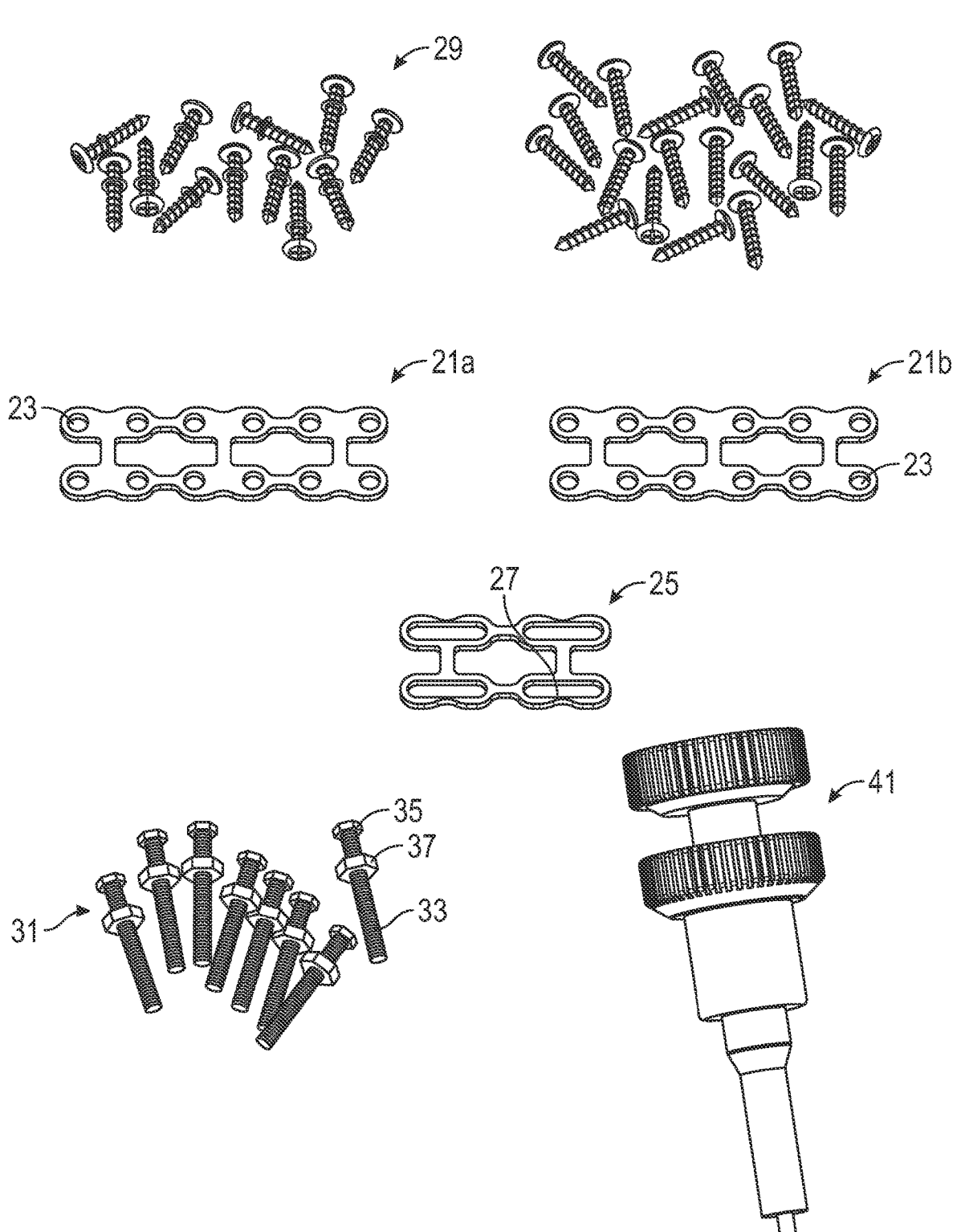
FIG. 3 is a view of parts needed for the sternal fracture fixation of the present disclosure.

FIG. 3 illustrates the hardware needed for the minimally invasive sternal fracture fixation, according to the present disclosure.

As shown, there are two rigid but bendable sternal plates 21*a*, 21*b* (or brackets), which are custom bent, if necessary, during an operation to fit the front surface of a sternum. Each of the sternal plates 21*a*, 21*b* has a plurality of threaded screw holes 23, as shown. In the preferred embodiment, the plurality of screw holes 23 are arranged in at least two parallel series.

A bridge plate 25 (or bracket) is used to bridge both of the sternal plates together. The bridge plate 25 contains a plurality of elongated sliding holes 27 (not threaded) that allow for adjustment, as will be described hereinafter. In the preferred embodiment, the plurality of screw holes 27 are arranged in at least two parallel series.

Further shown are broadhead locking screws 29. These broadhead locking screws 29 are used as the final lockdown screws for the bridge plate 25 and are used in the sliding holes 27 associated with the bridge plate 25.

There are elevating screws 31 (preferably, but not limited to, 3 mm diameter machine screws) with elevating nuts 37 that are used for elevating the depressed fragment of the sternum. These screws 31 each have elongated body 33 with machine threads, an Allen socket head 35, and an adjustable machine threaded nut 37. The elevating screws 31 are placed through the elongated sliding holes of the bridge plate 25 and temporarily lock into the screw holes of the sternal plates 21*a*, 21*b*. The adjustable elevating nut 37 is used to tighten the bridge plate 25 and one of the sternal plates 21*a*, 21*b* together, which in turn draws the affixed depressed sternal fragment and plate 21*a*, 21*b* into plane with the bridge plate 25 that is also affixed to the sternal plate 21*a*, 21*b* of the non-depressed sternal fragment.

The outer sternal plates 21*a*, 21*b* are threaded for both locking bone screws 29 and the temporary elevating screws 31 used for elevation of the depressed sternal fragment. The center bridge plate "slider" channels 27 are not threaded to allow the bridge plate 25 to slide, guided by the elevating screws 31.

Also shown is an elevating tool 41 that can be used in conjunction with the machine elevation screws 31 and nuts 37 to not only tighten the screws 31 but tighten the nuts 37, either independently or together. The elevating tool 41 is an optional feature. Other commercially available tools can be used instead of the tool 41 to accomplish similar results. Generally, in the preferred embodiment, the elevating tool 41 has an inner Allen wrench nested within an outer nut driver. The Allen wrench can be separated from the nut driver by pulling it out of the nut driver, but is designed to be operating while in the nested configuration so that this tool can be operated with a single hand of a surgeon to tighten both the machine screws and nuts, as will be further described hereafter.

Figure 4:
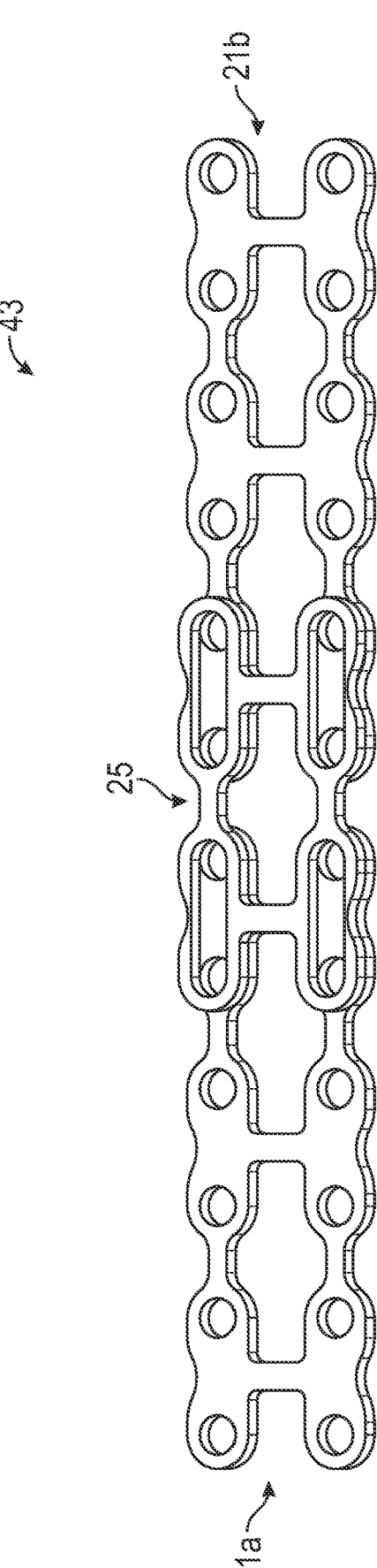
FIG. 4 is a view of the sternal plating construct that is created with the sternal plates and bridge plate of FIG. 3.
Figure 5:
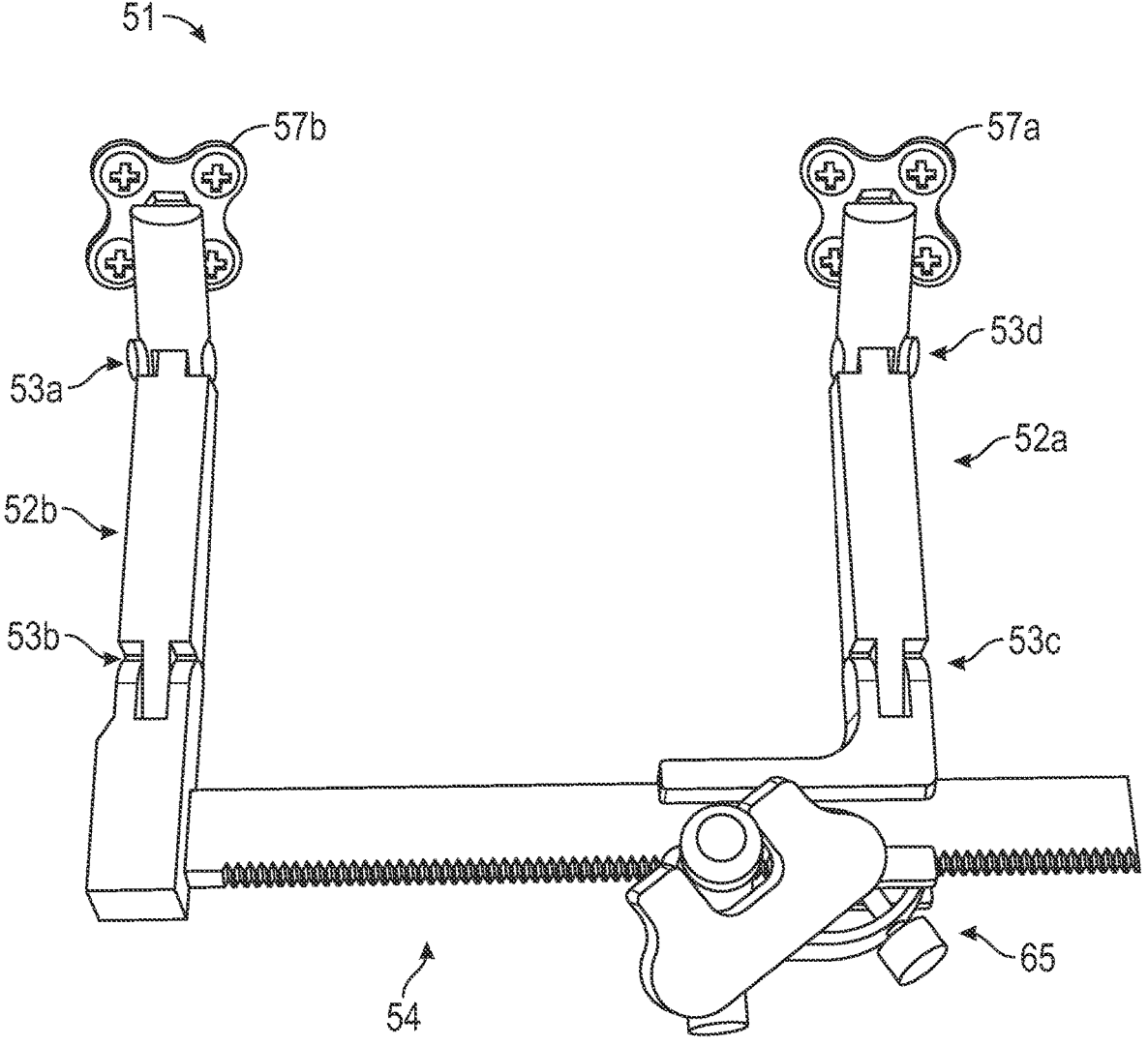
FIGS. 5 through 8 are views of a sternal retractor of the present disclosure that is used to install the sternal plating construct of FIG. 4.
Figure 6:
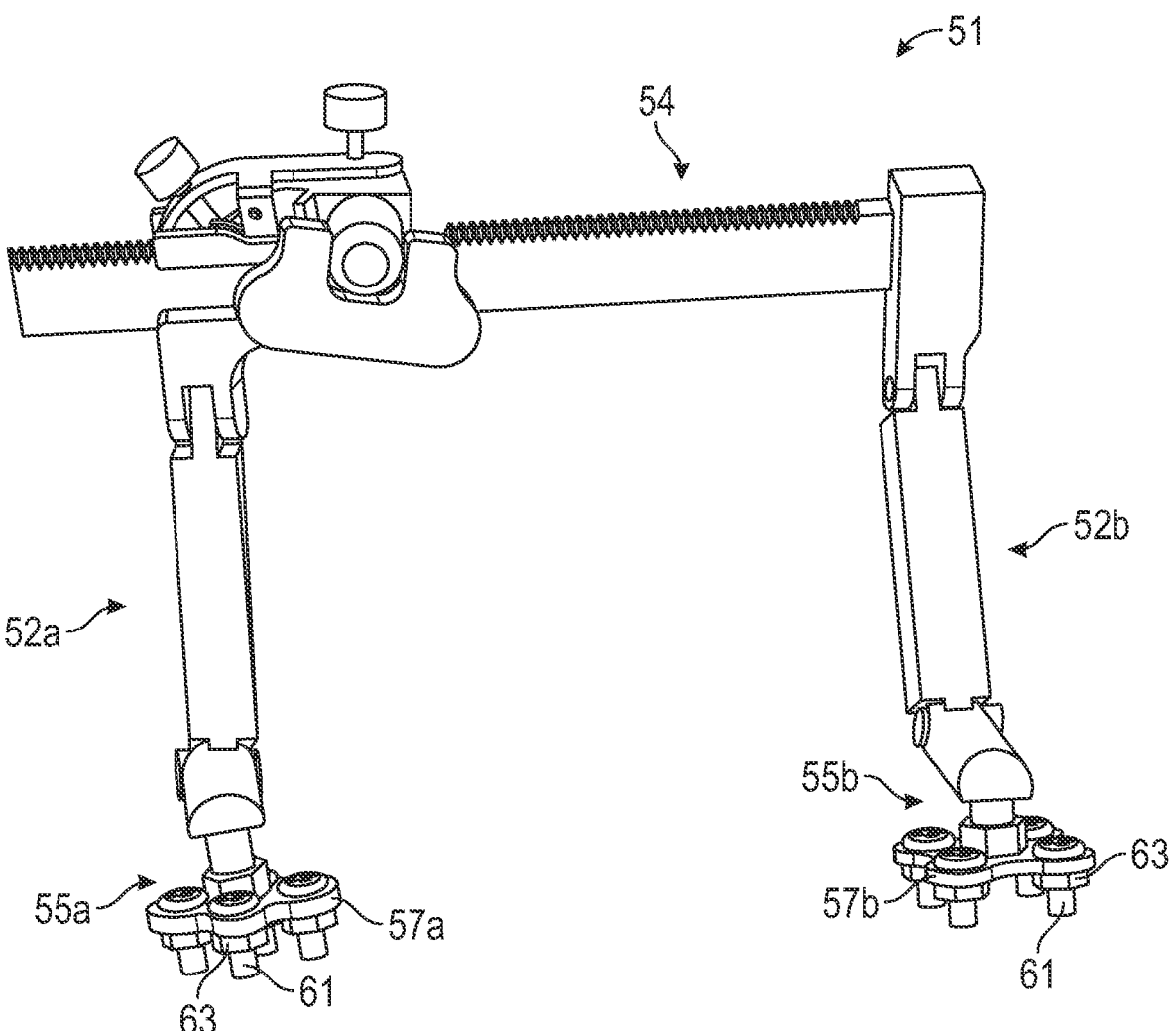
Figure 7:
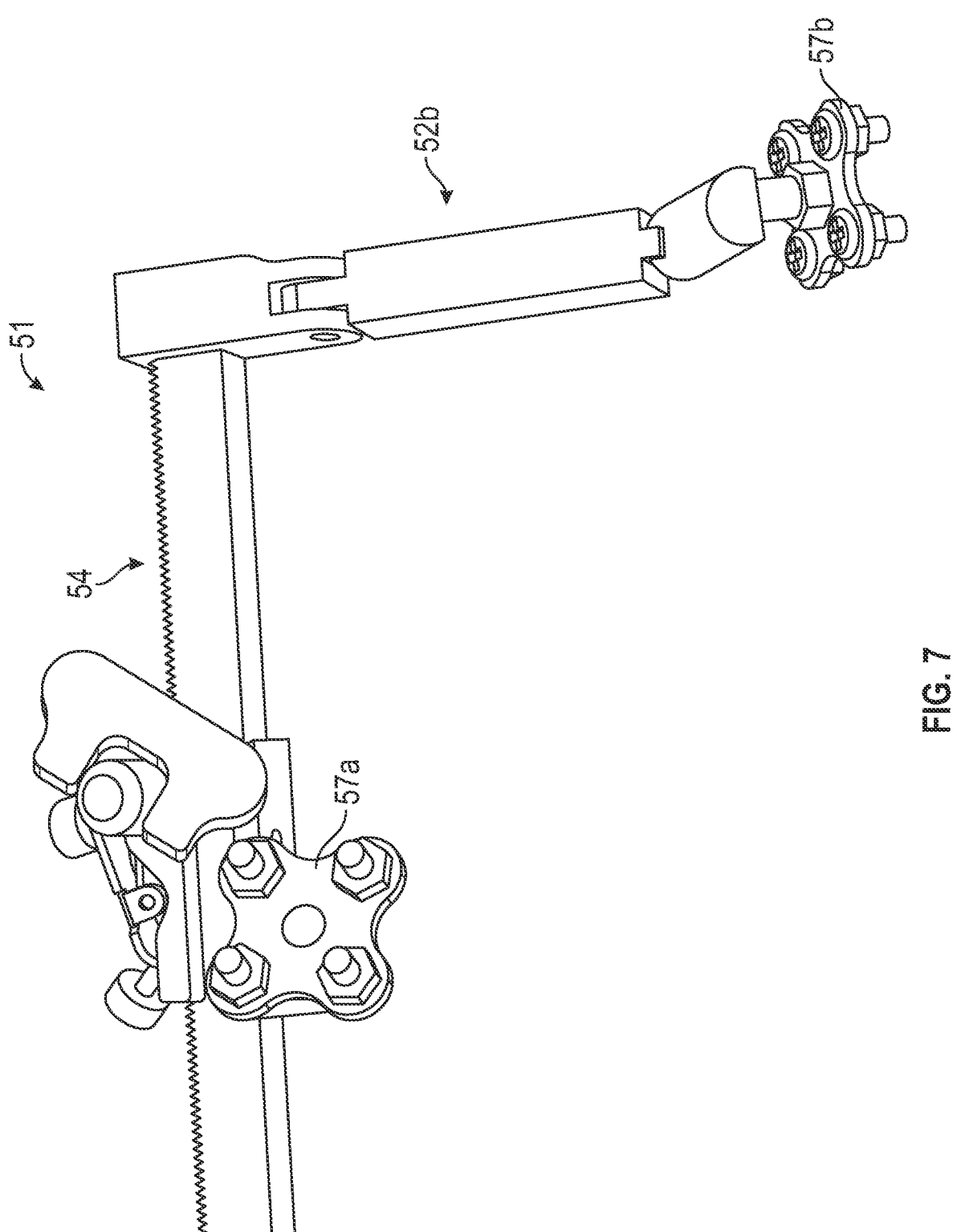
Figure 8:
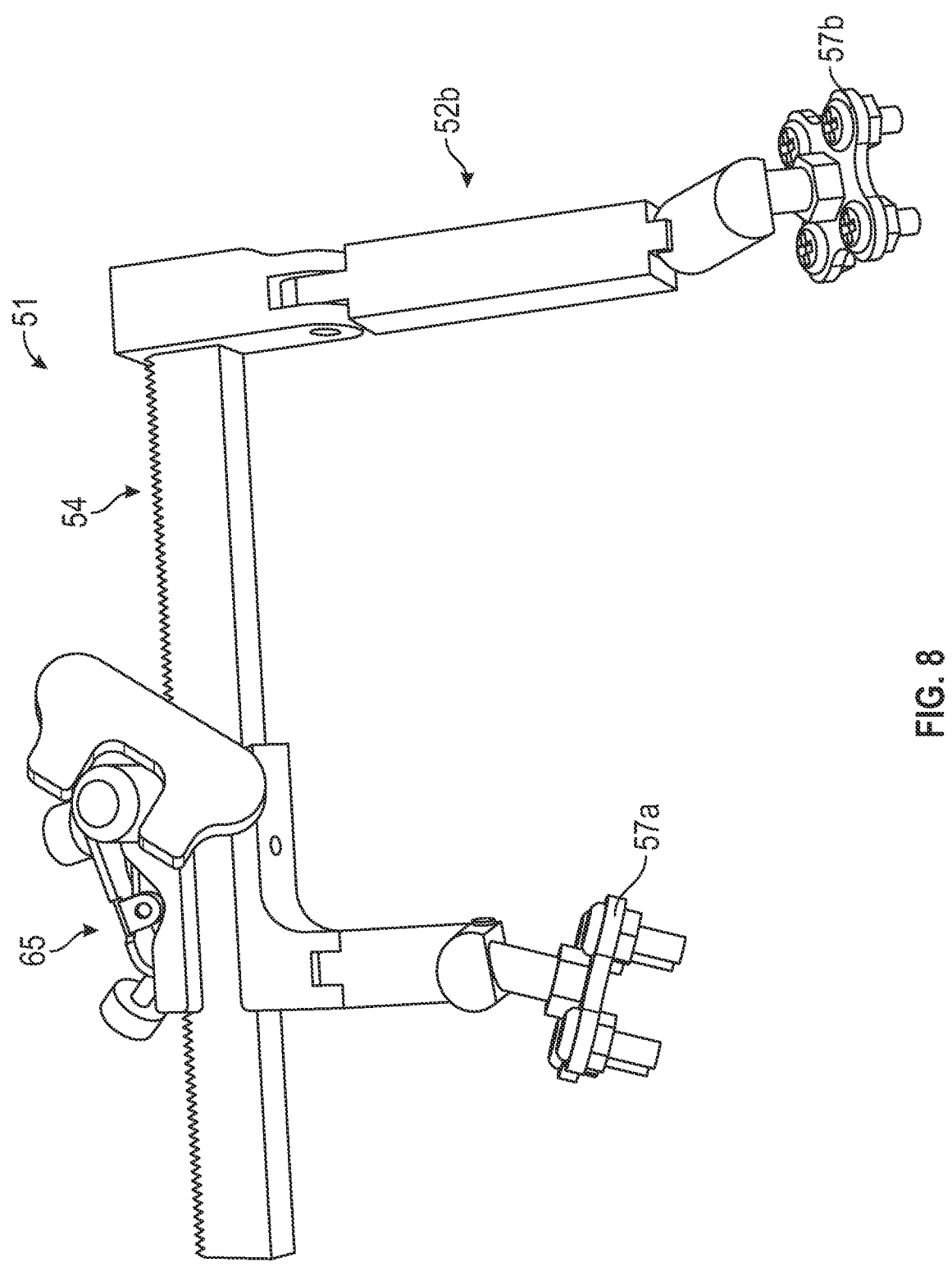

FIG. 4 illustrates the sternal plating construct 43. As shown, there are two sternal plates 21*a*, 21*b*, one to be placed on each side of the sternal fracture 11'. The bridge plate 25, which is the outwardly-positioned plate, is used to form a bridge between the two sternal plates 21*a*, 21*b* that can be used to not only slide back and forth to distract or compress the sternal fragments, but can also be used for additional adjustment, anterior to posterior, to elevate the sternal plate 21*a*, 21*b* that is depressed, along with the depressed sternal fragment. All three plates 21, 21*b*, 25 together, when locked in place, form one single sternal plate construct 43.

The first step in this medical procedure is to preconfigure and pre-bend a sternal plate 21*a*, 21*b* for each of the fractured sternal fragments. Each fragment has its own individual contours that need to be accounted for by each respective sternal plate 21*a*, 21*b*.

FIGS. 5-8 illustrate a sternal retractor 51 in accordance with the present disclosure. The sternal retractor 51 is placed into the incisional wound and is elevated at whatever angle is most convenient so that it can be controlled from outside of the wound. The sternal retractor 51 has a pair of extended arms 52*a*, 52*b* that extend from a lateral control arm 54. Each of the extended arms 52*a*, 52*b* has a plurality of arm members connected in a series via respective single axis arm joints 53*c*, 53*d* and 53*a*, 53*b*. Generally, the series of arm members has a distal end and a proximate end. Each of the arms 52*a*, 52*b* has a respective universal joint 55*a*, 55*b* at the respective distal end that connects to a respective foot plate 57*a*, 57*b*. The proximate ends of the arms 52*a*, 52*b* are attached to the lateral control arm 54.

Each of these foot plates 57*a*, 57*b* has a set of four wobble screws 61 (preferably, but not limited to, 3 mm diameter) with retaining nuts 63 (or clips) in corresponding slightly larger holes to enable the foot plate 57*a*, 57*b* to fit different contours as it is affixed temporarily to a sternal plate 21*a*, 21*b*. Note that the distance between these holes will change if there is a bend in the sternal plate 21*a*, 21*b*. Retaining nuts 63 (or clips) prevent the wobble screws 61 from falling out and keep them intact with a foot plate 57*a*, 57*b* of the sternal retractor 51 at all times, whether they are also temporarily affixed to the main sternal plate 21*a*, 21*b* or detached from it. The multiple joints and wobble screws together allow complete mobility of the sternal plate 21*a*, 21*b* that is placed into random planes within the sternal fracture. The sternal retractor 51 has a significant amount of built in adjustability.

The sternal retractor 51 has a ratchet mechanism 65 that locks a rack and pinion in place to prevent relative movement of the arms 52*a*, 52*b*. By using the controls, the rack and opinion can be unlocked and moved in either direction in order to either open or close (i.e., further separate or bring together arms 52*a*, 52*b*) the sternal retractor 51 to distract or compress the sternal fragments, respectively.

Figure 9:
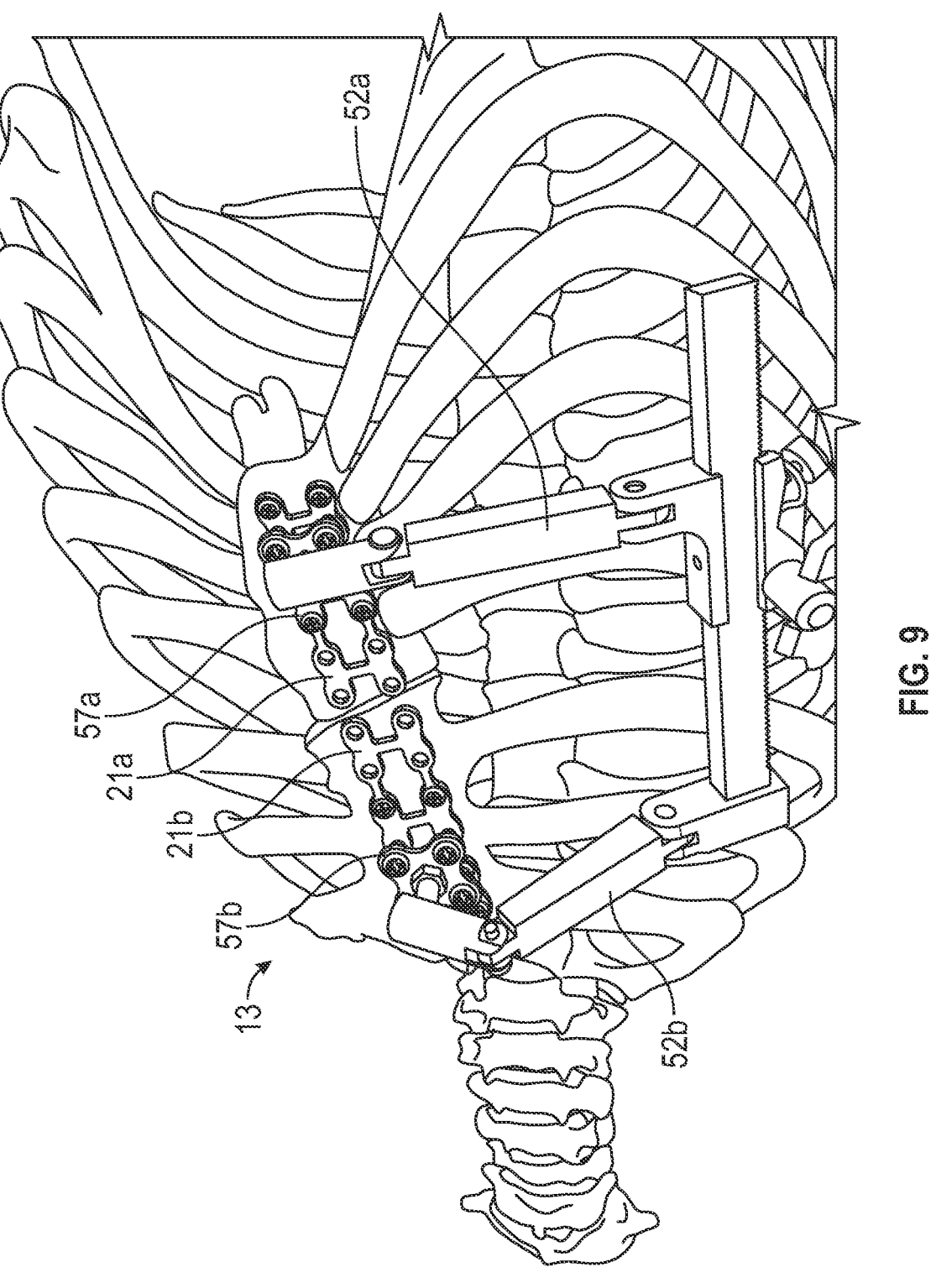
FIGS. 9 through 11 are views showing installation of the sternal plating construct of FIG. 4 using the sternal retractor of FIGS. 5 through 8.

FIG. 9 illustrates how the sternal plates 21*a*, 21*b* are temporarily affixed to respective foot plates 57*a*, 57*b* of the sternal retractor 51 and how the sternal plates 21*a*, 21*b* (guided by the foot plates 56*a*, 57*b*) are placed in the area of the sternum that is likely not involved with the fracture, as the fracture would be centered between the sternal plates 21*a*, 21*b*. A few screw holes are left on either side of the sternal plates 21*a*, 21*b* so that each sternal plate can be mounted to the sternum while the sternal retractor 51 is still affixed to it. Note that there is complete 360-degree range of mobility for each of these sternal plates 21*a*, 21*b* so that random configurations that occur with traumatic fracture of the sternum can be addressed.

Figure 10:
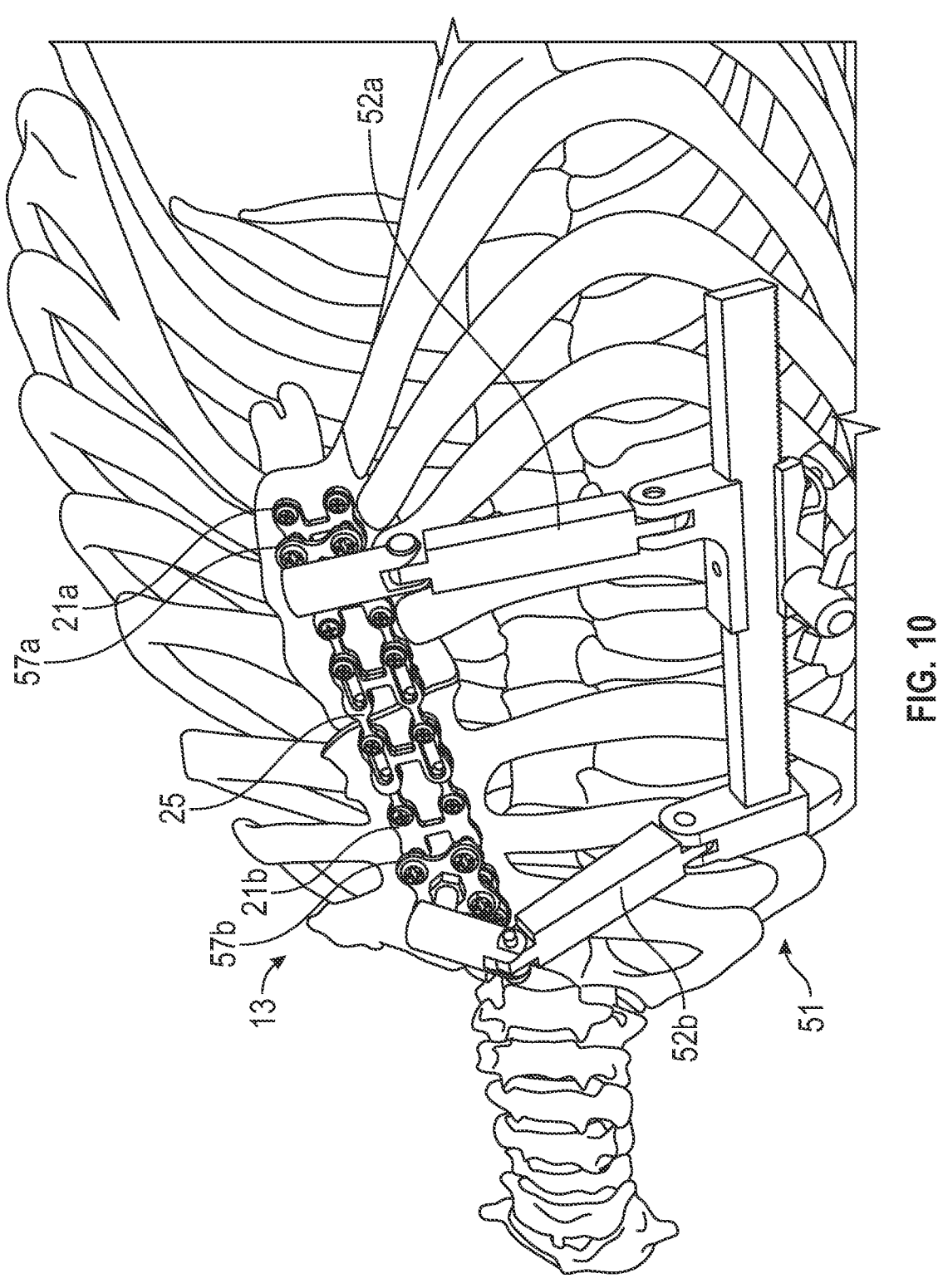

FIG. 10 shows the sternal retractor 51 and sternal plate construct 43 (FIG. 4) in place on the sternum. There have been four locking screws 29 (FIG. 3) placed through each of the sternal plates 21*a*, 21*b*. This sufficiently affixes the retractor 51 and the plate construct 43 securely enough so that manipulation of the sternal fracture can take place. With the ratchet open on the sternal retractor 51, the surgeon can compress or distract as desired. Note that this only compresses and distracts. An elevation mechanism is employed with elevating screws 31 (FIG. 3). Therefore, if the sternal fragments are telescoped into each other, they can be distracted and separated appropriately, so the surgeon can then provide elevation and later compress the fragments back together once they are in proper plane.

Figure 11:
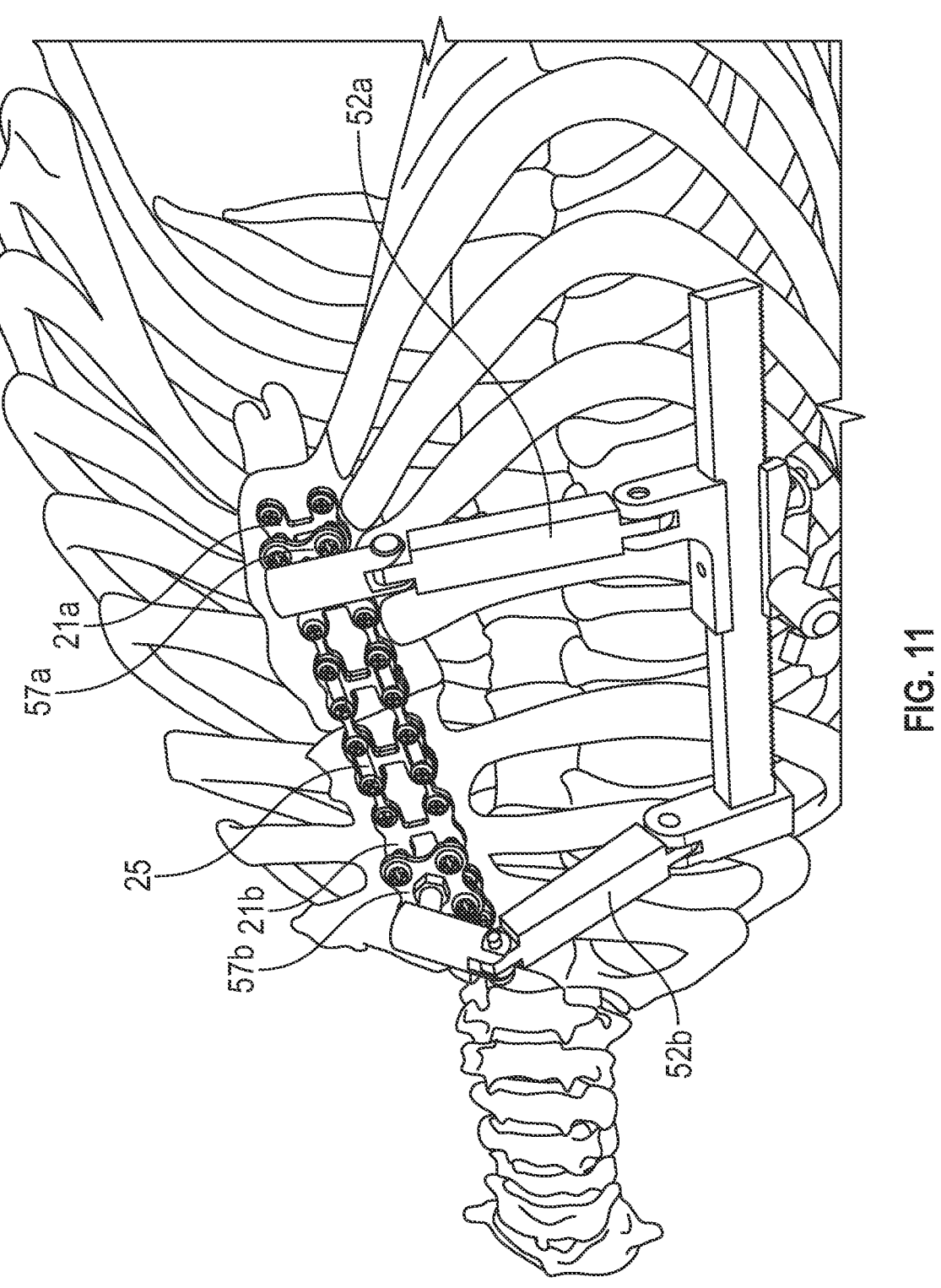

FIG. 11 illustrates the sternal fragments being compressed. Note that the arms 52a, 52b of the sternal retractor 51 are in a slightly irregular configuration, which would be normal with the random configuration of a fracture. The universal joint 55a, 55b of the foot plates 57a, 57b and the multiple joints 53a-53d in the retractor arms 52a, 52b compensate for this and allow the retractor 51 to be placed in a suitable position. The bridge plate 25 is then placed over and onto the aligned sternal plates 21a, 21b. At least two of the elevating screws 31 (FIG. 3) and nuts 37 are placed through the bridge plate and into each of the sternal plates 21a, 21b on each of the fragments as the anatomy allows. The bridge plate 25 can still be adjusted in the superior and inferior directions. Once in place, the bridge plate 25 and elevating screws 31 and nuts 37 can allow the surgeon to elevate a depressed sternal fragment.

As previously described, the elevating tool 41 has an Allen wrench and a nut driver. The Allen wrench is placed into the elevating screw 31 and held while the nut driver is used to tighten the nut on the screw in order to tighten the bridge plate 25 up against the non-depressed sternal plate. As this is done, it flattens the bridge plate 25 up against the more elevated sternal fragment, i.e., the one that is not depressed. As the opposing elevating nuts 37 are tightened toward the depressed fragment, using the bridge plate 25 as a fulcrum, it will draw the depressed fragment up along with its sternal plate 21a, 21b into the same plane as the non-depressed main sternal plate 21b, 21a, thus elevating the depressed fragment. Additional adjustment can be accomplished by unlocking the rachet mechanism 65 on the retractor and placing it in a bidirectional configuration. Now, the surgeon can compress or distract, as desired. Minor further adjustment may be necessary with basic surgical hand instruments. Note that this elevating tool can be used with one hand and takes the place of at least two tools. Minor adjustments have now been made to draw these three plates into better alignment with each other. Afterward, the bridge plate is retightened against the sternal plates.

Next, four locking broadhead screws 29 (FIG. 3) are then placed into the open sliding holes within the bridge plate 25 and placed into the sternum. These are locked down tightly. The elevating screws 31 are then removed by loosening the elevating nuts 37 and using the Allen wrench of the elevating tool 41 to rotate the elevating screws outwardly. The remaining broadhead locking screws 29 are then placed through the same holes that originally were occupied by the elevating screws 31, as shown in FIG. 11.

While in the foregoing specification, this invention has been described in relation to certain embodiments thereof, such as preferred embodiments, and many details have been put forth for the purpose of illustration, it will be apparent to those skilled in the art that the invention provides many additional embodiments, that any preferred embodiments are merely nonlimiting examples, and that certain of the details described herein can be varied considerably without departing from the basic principles of the invention.

At least the following is claimed:

1. An apparatus for repairing a fractured sternum having first and second sternal parts separated by a fracture, the apparatus comprising:

a first sternal plate, the first sternal plate having an elongated body with opposing sides that are generally planar, the opposing sides having a periphery defined by opposing side edges and opposing ends, the elongated body having a plurality of screw holes, the first sternal plate configured to be attached to the first sternal part via screws installed in the screw holes;

a second sternal plate, the second sternal plate having an elongated body with opposing sides that are generally planar, the opposing sides having a periphery defined by opposing side edges and opposing ends, the elongated body having a plurality of screw holes, the second sternal plate configured to be attached to the second sternal part via screws installed in the screw holes;

a bridge plate having an elongated body with opposing sides that are generally planar, the opposing sides having a periphery defined by opposing side edges and opposing ends, the elongated body having a plurality of screw holes, the bridge plate overlapping respective parts of the first and second sternal plates so that its plurality of screw holes is in sufficient alignment with underlying screw holes associated with the first and second sternal plates to enable the bridge plate to be installed over the sternal plates via screws; and wherein each of the bridge plate and the first and second sternal plates comprise two parallel series of screw holes.

2. The apparatus of claim 1, wherein the first and second sternal plates and the bridge plate are rigid, but bendable.

3. The apparatus of claim 1, wherein the plurality of screw holes associated with the bridge plate are elongated to enable movement of the bridge plate relative to both the first and second sternal plates while enabling sufficient alignment of the screw holes of the bridge plate with underlying screw holes associated with the first and second sternal plates.

4. An adjustable sternal plate apparatus for fixating and repairing a fractured sternum having first and second sternal parts separated by a fracture, comprising:

a first sternal plate, the first sternal plate having an elongated body with opposing sides that are generally planar, the opposing sides having a periphery defined by opposing side edges and opposing ends, the elongated body having a plurality of screw holes, the first sternal plate attachable to the first sternal part via screws installed in the screw holes;

a second sternal plate, the second sternal plate having an elongated body with opposing sides that are generally planar, the opposing sides having a periphery defined by opposing side edges and opposing ends, the elongated body having a plurality of screw holes, the second sternal plate attachable to the second sternal part via screws installed in the screw holes;

a bridge plate having an elongated body with opposing sides that are generally planar, the opposing sides having a periphery defined by opposing side edges and opposing ends, the elongated body having a plurality of elongated screw holes, the bridge plate for overlapping respective parts of the first and second sternal plates so that its plurality of elongated screw holes is in sufficient alignment with underlying screw holes associated with the first and second sternal plates to enable the bridge plate to be installed over the sternal plates via screws; and wherein each of the bridge plate and the first and second sternal plates comprise two parallel series of screw holes.

5. The apparatus of claim 4, wherein the first and second sternal plates and the bridge plate are rigid, but bendable.

6. An adjustable sternal plate apparatus for fixating and repairing a fractured sternum having first and second sternal parts separated by a fracture, comprising:

a first sternal plate, the first sternal plate having an elongated body with opposing sides that are generally planar, the opposing sides having a periphery defined by opposing side edges and opposing ends, the elongated body having a plurality of screw holes, the first sternal plate attachable to the first sternal part via screws installed in the screw holes;

a second sternal plate, the second sternal plate having an elongated body with opposing sides that are generally planar, the opposing sides having a periphery defined by opposing side edges and opposing ends, the elongated body having a plurality of screw holes, the second sternal plate attachable to the second sternal part via screws installed in the screw holes; and a bridge plate having an elongated body with opposing sides that are generally planar, the opposing sides having a periphery defined by opposing side edges and opposing ends, the elongated body having a plurality of elongated screw holes, the bridge plate for overlapping respective parts of the first and second sternal plates so that its plurality of elongated screw holes is in sufficient alignment with underlying screw holes associated with the first and second sternal plates to enable the bridge plate to be installed over the sternal plates via screws;

a first plurality of screws extending through the first sternal plate and under the first sternal plate for penetration into the first sternal part to thereby attach the first sternal plate to the first sternal part;

a second plurality of screws extending through the second sternal plate and under the second sternal plate for penetration into the second sternal part to thereby attach the second sternal plate to the second sternal part;

a third plurality of screws extending through the bridge plate, through the first sternal plate, and under the bridge plate for penetration into the first sternal part to thereby attach both the bridge plate and the first sternal plate to the first sternal part; and a fourth plurality of screws extending through the bridge plate, through the second sternal plate, and under the bridge plate for penetration into the second sternal part to thereby attach both the bridge plate and the second sternal plate to the second sternal part.

7. A method for repairing a sternum fracture, comprising the steps of:

(a) providing an adjustable sternal plate apparatus for fixating and repairing a fractured sternum having first and second sternal parts separated by a fracture, comprising:

(1) a first sternal plate, the first sternal plate having an elongated body with opposing sides that are generally planar, the opposing sides having a periphery defined by opposing side edges and opposing ends, the elongated body having a plurality of screw holes, the first sternal plate attachable to the first sternal part via screws installed in the screw holes;

(2) a second sternal plate, the second sternal plate having an elongated body with opposing sides that are generally planar, the opposing sides having a periphery defined by opposing side edges and opposing ends, the elongated body having a plurality of screw holes, the second sternal plate attachable to the second sternal part via screws installed in the screw holes; and (3) a bridge plate having an elongated body with opposing sides that are generally planar, the opposing sides having a periphery defined by opposing side edges and opposing ends, the elongated body having a plurality of elongated screw holes, the bridge plate for overlapping respective parts of the first and second sternal plates so that its plurality of elongated screw holes is in sufficient alignment with underlying screw holes associated with the first and second sternal plates to enable the bridge plate to be installed over the sternal plates via screws;

(b) providing a sternal retractor comprising:

(1) a first arm, the first arm having a plurality of elongated first arm members connected together in a first series via a plurality of single axis joints, the first series having a distal end and a proximal end, the first arm having a first foot plate attached to the distal end via a first universal joint, the first foot plate having a means for detachably mounting the first arm to a first sternal plate;

(2) a second arm, the second arm having a plurality of elongated second arm members connected together in a second series via a plurality of single axis joints, the second series having a distal end and a proximate end, the second arm having a second foot plate attached to the distal end via a second universal joint, the second foot plate having a means for detachably mounting the second arm to a second sternal plate; and (3) a lateral control arm that connects to the first and second arms at their respective proximate ends, the lateral control arm having a rack and pinion mechanism that enables lateral movement of the lateral control arm to shorten and lengthen a lateral distance between the first and second arms, the rack and pinion mechanism capable of being locked and unlocked to prevent and permit the lateral movement, (a) temporarily attaching the first and second foot plates of the sternal retractor to the first and second sternal plates, respectively;

(b) mounting the first and second sternal plates to respective first and second parts of the fractured sternum;

(c) aligning the first and second parts of the fractured sternum by adjusting the sternal retractor;

(d) mounting the bridge plate over the first and second sternal plates to secure together the bridge plate, the first and second sternal plates, and the first and second sternal parts; and (e) de-attaching the sternal retractor from the first and second sternal plates.

8. The method of claim 7, wherein the means for detachably mounting that is associated with each of the foot plates includes a plurality of wobble screws in corresponding slightly larger holes to enable the foot plates to be able to fit different contours as the foot plates are affixed temporarily to respective sternal plates.

9. A method for repairing a sternum fracture, comprising the steps of:

(a) providing an adjustable sternal plate apparatus for fixating and repairing a fractured sternum having first and second sternal parts separated by a fracture, comprising:

(1) a first sternal plate, the first sternal plate having an elongated body with opposing sides that are generally planar, the opposing sides having a periphery defined by opposing side edges and opposing ends, the elongated body having a plurality of screw holes, the first sternal plate attachable to the first sternal part via screws installed in the screw holes;

(2) a second sternal plate, the second sternal plate having an elongated body with opposing sides that are generally planar, the opposing sides having a periphery defined by opposing side edges and opposing ends, the elongated body having a plurality of screw holes, the second sternal plate attachable to the second sternal part via screws installed in the screw holes; and (3) a bridge plate having an elongated body with opposing sides that are generally planar, the opposing sides having a periphery defined by opposing side edges and opposing ends, the elongated body having a plurality of elongated screw holes, the bridge plate for overlapping respective parts of the first and second sternal plates so that its plurality of elongated screw holes is in sufficient alignment with underlying screw holes associated with the first and second sternal plates to enable the bridge plate to be installed over the sternal plates via screws;

(b) mounting the first and second sternal plates to respective first and second parts of the fractured sternum;

(c) aligning the first and second parts of the fractured sternum; and (d) mounting the bridge plate over the first and second sternal plates to secure together the bridge plate, the first and second sternal plates, and the first and second sternal parts.

10. The method of claim 9, wherein one of the sternal parts and corresponding sternal plates is depressed and another of the sternal parts and corresponding sternal plates is non-depressed and further comprising the step of:

aligning the first and second parts of the fractured sternum by tightening screws extending through the bridge plate and the non-depressed sternal plate.

11. The method of claim 10, further comprising the step of:

mounting the first and second sternal plates by installing a plurality of elevating screws with corresponding nuts; and tightening at least one of the elevating screws with corresponding nuts in order to move the bridge plate against the non-depressed sternal plate, thereby causing the depressed sternal plate and a corresponding depressed sternal fragment to elevate into a plane associated with the non-depressed sternal plate.

12. A method for fixating and repairing a sternum fracture, the method comprising the steps of:

(a) providing three plates, including a bridge plate, a first sternal plate, and a second sternal plate, each plate having a plurality of screw holes;

(b) mounting the first and second sternal plates to respective first and second parts of the fractured sternum on separate sides of the fracture by installing screws through the first and second sternal plates into the respective first and second parts; and (c) mounting the bridge plate over the first and second sternal plates by installing screws through the bride plate and the first and second sternal plates in order to secure together the bridge plate, the first and second sternal plates, and the first and second sternal parts;

wherein the plurality of holes associated with each plate are arranged in at least two parallel series.

13. A method for fixating and repairing a sternum fracture, the method comprising:

(a) providing three plates, including a bridge plate, a first sternal plate, and a second sternal plate, each plate having a plurality of screw holes;

(b) mounting the first and second sternal plates to respective first and second parts of the fractured sternum on separate sides of the fracture by installing screws through the first and second sternal plates into the respective first and second parts; and (c) mounting the bridge plate over the first and second sternal plates by installing screws through the bride plate and the first and second sternal plates in order to secure together the bridge plate, the first and second sternal plates, and the first and second sternal parts; and and further comprising:

(a) providing a sternal retractor comprising:

(1) a first arm, the first arm having a plurality of elongated first arm members connected together in a first series via a plurality of single axis joints, the first series having a distal end and a proximal end, the first arm having a first foot plate attached to the distal end via a first universal joint, the first foot plate having a means for detachably mounting the first arm to a first sternal plate;

(2) a second arm, the second arm having a plurality of elongated second arm members connected together in a second series via a plurality of single axis joints, the second series having a distal end and a proximate end, the second arm having a second foot plate attached to the distal end via a second universal joint, the second foot plate having a means for detachably mounting the second arm to a second sternal plate; and (3) a lateral control arm that connects to the first and second arms at their respective proximate ends, the lateral control arm having a rack and pinion mechanism that enables lateral movement of the lateral control arm to shorten and lengthen a lateral distance between the first and second arms, the rack and pinion mechanism capable of being locked and unlocked to prevent and permit the lateral movement, (b) temporarily attaching the first and second foot plates of the sternal retractor to the first and second sternal plates, respectively;

(c) mounting the first and second sternal plates to the respective first and second parts of the fractured sternum with assistance of the sternal retractor;

(d) aligning the first and second parts of the fractured sternum with assistance from and by adjusting the sternal retractor;

(e) with assistance from the sternal retractor, mounting the bridge plate over the first and second sternal plates to secure together the bridge plate, the first and second sternal plates, and the first and second sternal parts; and (f) de-attaching the sternal retractor from the first and second sternal plates.

14. The method of claim 13, further comprising the step of permitting one or more of the first and second sternal plates to bend while performing the aligning step.

15. A method for fixating and repairing a sternum fracture, the method comprising the steps of:

(a) providing three plates, including a bridge plate, a first sternal plate, and a second sternal plate, each plate having a plurality of screw holes;

(b) mounting the first and second sternal plates to respective first and second parts of the fractured sternum on separate sides of the fracture by installing screws through the first and second sternal plates into the respective first and second parts; and (c) mounting the bridge plate over the first and second sternal plates by installing screws through the bride plate and the first and second sternal plates in order to secure together the bridge plate, the first and second sternal plates, and the first and second sternal parts;

wherein the means for detachably mounting that is associated with each of the foot plates includes a plurality of wobble screws in corresponding slightly larger holes to enable the foot plates to be able to fit different contours as the foot plates are affixed temporarily to respective sternal plates.

16. A method for fixating and repairing a sternum fracture, the method comprising the steps of:

(a) providing three plates, including a bridge plate, a first sternal plate, and a second sternal plate, each plate having a plurality of screw holes;

(b) mounting the first and second sternal plates to respective first and second parts of the fractured sternum on separate sides of the fracture by installing screws through the first and second sternal plates into the respective first and second parts; and (c) mounting the bridge plate over the first and second sternal plates by installing screws through the bride plate and the first and second sternal plates in order to secure together the bridge plate, the first and second sternal plates, and the first and second sternal parts;

and further comprising the steps of:

installing a first plurality of screws extending through the first sternal plate and under the first sternal plate for penetration into the first sternal part to thereby attach the first sternal plate to the first sternal part;

installing a second plurality of screws extending through the second sternal plate and under the second sternal plate for penetration into the second sternal part to thereby attach the second sternal plate to the second sternal part;

installing a third plurality of screws extending through the bridge plate, through the first sternal plate, and under the bridge plate for penetration into the first sternal part to thereby attach both the bridge plate and the first sternal plate to the first sternal part; and installing a fourth plurality of screws extending through the bridge plate, through the second sternal plate, and under the bridge plate for penetration into the second sternal part to thereby attach both the bridge plate and the second sternal plate to the second sternal part.

17. A method for fixating and repairing a sternum fracture, the method comprising the steps of:

(a) providing three plates, including a bridge plate, a first sternal plate, and a second sternal plate, each plate having a plurality of screw holes;

(b) mounting the first and second sternal plates to respective first and second parts of the fractured sternum on separate sides of the fracture by installing screws through the first and second sternal plates into the respective first and second parts; and (c) mounting the bridge plate over the first and second sternal plates by installing screws through the bride plate and the first and second sternal plates in order to secure together the bridge plate, the first and second sternal plates, and the first and second sternal parts;

wherein one of the sternal parts and corresponding sternal plates is depressed and another of the sternal parts and corresponding sternal plates is non-depressed and further comprising the step of:

(d) aligning the first and second parts of the fractured sternum with screws extending through the bridge plate and the depressed sternal plate by tightening respective nuts situated on the screws.

* * * * *